(12) United States Patent
Saikou

(10) Patent No.: US 12,082,770 B2
(45) Date of Patent: Sep. 10, 2024

(54) LOCATION ESTIMATION APPARATUS, LOCATION ESTIMATION METHOD, AND COMPUTER READABLE RECORDING MEDIUM

(71) Applicant: NEC Corporation, Tokyo (JP)

(72) Inventor: Masahiro Saikou, Tokyo (JP)

(73) Assignee: NEC CORPORATION, Tokyo (JP)

(*) Notice: Subject to any disclaimer, the term of this patent is extended or adjusted under 35 U.S.C. 154(b) by 635 days.

(21) Appl. No.: 17/277,158

(22) PCT Filed: Aug. 16, 2019

(86) PCT No.: PCT/JP2019/032190
§ 371 (c)(1),
(2) Date: Mar. 17, 2021

(87) PCT Pub. No.: WO2020/059377
PCT Pub. Date: Mar. 26, 2020

(65) Prior Publication Data
US 2022/0000338 A1    Jan. 6, 2022

(30) Foreign Application Priority Data
Sep. 20, 2018  (JP) ................. 2018-175740

(51) Int. Cl.
*G06T 7/73*    (2017.01)
*A61B 1/00*    (2006.01)
(Continued)

(52) U.S. Cl.
CPC .... *A61B 1/000094* (2022.02); *A61B 1/00045* (2013.01); *A61B 1/31* (2013.01);
(Continued)

(58) Field of Classification Search
CPC ... A61B 1/000094; A61B 1/0004; A61B 1/31; G06T 7/74; G06T 7/50; G06T 7/0012; G06T 2207/30028
See application file for complete search history.

(56) References Cited

U.S. PATENT DOCUMENTS 7,630,148 B1 * 12/2009 Yang .................... G02B 23/243
                                                           359/740
7,961,401 B1 *  6/2011 Scott ....................... G02B 7/10
                                                           359/676
(Continued)

FOREIGN PATENT DOCUMENTS

JP    2002-000546 A    1/2002
JP    2003-265408 A    9/2003
(Continued)

OTHER PUBLICATIONS

Extended European Search Report for EP Application No. EP19861418.2 dated on Sep. 21, 2021.
(Continued)

*Primary Examiner* — Kevin Ky

(57) ABSTRACT

A location estimation apparatus 1 includes: a feature amount extraction unit 2 configured to extract, a feature amount of a living-body internal image, from the living-body internal image captured using an endoscope; a similarity degree output unit 3 configured to output similarity degrees with a plurality of locations inside a living body using the feature amount; and an estimation unit 4 configured to estimate a location of the captured living-body internal image inside the living body using the similarity degrees.

9 Claims, 10 Drawing Sheets

(51) Int. Cl.
*A61B 1/31* (2006.01)
*G06T 7/00* (2017.01)
*G06T 7/50* (2017.01)

(52) U.S. Cl.
CPC .............. *G06T 7/0012* (2013.01); *G06T 7/50* (2017.01); *G06T 7/74* (2017.01); *G06T 2207/30028* (2013.01)

(56) References Cited

U.S. PATENT DOCUMENTS

| | | | |
|---|---|---|---|
| 11,721,020 B2* | 8/2023 | Ben-Haim | G06T 3/067 |
| | | | 382/128 |
| 2007/0288043 A1* | 12/2007 | Rehnke | A61B 17/320036 |
| | | | 606/170 |
| 2008/0008368 A1* | 1/2008 | Matsumoto | G06T 19/00 |
| | | | 382/128 |
| 2009/0227837 A1* | 9/2009 | Shimizu | A61B 1/0684 |
| | | | 600/109 |
| 2009/0247992 A1* | 10/2009 | Shalon | A61F 2/2476 |
| | | | 606/1 |
| 2009/0290162 A1* | 11/2009 | Erkmen | A61B 5/0066 |
| | | | 356/450 |
| 2010/0286791 A1* | 11/2010 | Goldsmith | A61B 17/12022 |
| | | | 604/524 |
| 2014/0150804 A1* | 6/2014 | Shalon | A61F 5/566 |
| | | | 128/848 |
| 2014/0163664 A1* | 6/2014 | Goldsmith | A61B 17/0057 |
| | | | 604/93.01 |
| 2014/0275986 A1* | 9/2014 | Vertikov | A61B 5/062 |
| | | | 600/424 |
| 2014/0276108 A1* | 9/2014 | Vertikov | A61B 5/0066 |
| | | | 600/478 |
| 2015/0057498 A1 | 2/2015 | Akimoto et al. | |
| 2015/0313445 A1* | 11/2015 | Davidson | A61B 1/31 |
| | | | 600/109 |
| 2015/0359418 A1* | 12/2015 | Feussner | A61B 5/055 |
| | | | 600/111 |
| 2016/0287141 A1* | 10/2016 | Sidlesky | G02B 23/2415 |
| 2016/0292498 A1 | 10/2016 | Miura | |
| 2016/0309992 A1* | 10/2016 | Stith | A61B 1/0005 |
| 2017/0071504 A1 | 3/2017 | Wang | |
| 2018/0098685 A1 | 4/2018 | Osawa | |
| 2022/0000338 A1* | 1/2022 | Saikou | G06T 7/50 |

FOREIGN PATENT DOCUMENTS

| | | |
|---|---|---|
| JP | 2009-056239 A | 3/2009 |
| JP | 2009-213627 A | 9/2009 |
| JP | 2011-050590 A | 3/2011 |
| JP | 2012-024518 A | 2/2012 |
| JP | 2016-189812 A | 11/2016 |
| JP | 2017-055954 A | 3/2017 |
| WO | 2017/006449 A1 | 1/2017 |
| WO | 2018/012080 A1 | 1/2018 |

OTHER PUBLICATIONS

International Search Report for PCT Application No. PCT/JP2019/032190, mailed on Oct. 8, 2019.

Timo Ojala et al., "Performance Evaluation of Texture Measures with Classification Based on Kullback Discrimination of Distributions", Proceeding of IEEE International Conference Pattern Recognition, 1994, pp. 562-585.

K. Karsch et al., "Depth extraction from video using nonparametric sampling", European Conference on Computer Vision. Springer, 2012, pp. 775-788.

English translation of Written opinion for PCT Application No. PCT/JP2019/032190, mailed on Oct. 8, 2019.

* cited by examiner

A CECUM

B ASCENDING COLON

C TRANSVERSE COLON

D DESCENDING COLON

Fig.4

| IDENTIFICATION INFORMATION | SIMILARITY DEGREE |
|---|---|
| CECUM | 0.1 |
| ASCENDING COLON | 0.9 |
| TRANSVERSE COLON | 0.5 |
| DESCENDING COLON | 0.2 |
| ⋮ | ⋮ |

LOCATION ESTIMATION APPARATUS, LOCATION ESTIMATION METHOD, AND COMPUTER READABLE RECORDING MEDIUM

This application is a National Stage Entry of PCT/JP2019/032190 filed on Aug. 16, 2019, which claims priority from Japanese Patent Application 2018-175740 filed on Sep. 20, 2018, the contents of all of which are incorporated herein by reference, in their entirety.

TECHNICAL FIELD

The present invention relates to a location estimation apparatus and location estimation method for estimating an image capture location inside a living body, and further relates to a computer readable recording medium that includes recorded thereon a program for realizing the location estimation apparatus and the location estimation method.

BACKGROUND ART

In a case in which images of the inside of a living body are captured during a surgery, it would be desirable if an observer could accurately find out, in real time, the location inside the living body corresponding to the current image capture location. This is because the observer relies on captured images of the inside of the living body in carrying out the surgery.

In view of this situation, a technique is proposed for allowing an observer to find out which location inside a living body an image is being captured of. For example, a device that captures an image of the shape of an insertion unit of an endoscope using an X-ray examination device, and a device that detects the location and orientation of an image-capturing unit of an endoscope using a magnetic resonance image diagnosis device are being proposed.

Furthermore, as a related technique, Patent Document 1 discloses an endoscopic device that accurately detects the location of an image-capturing unit (the distal end of an insertion unit of an endoscope). According to this endoscopic device, the location of the distal end and the shape of the insertion unit are specified by driving a plurality of transmission coils that are provided in the insertion unit and detecting magnetic fields generated by the transmission coils.

LIST OF RELATED ART DOCUMENTS

Patent Document

Patent Document 1: Japanese Patent Laid-Open Publication No. 2002-000546

SUMMARY

Technical Problems

However, the above-described techniques make surgery cumbersome since the location of the image-capturing unit and the shape of the insertion unit of the endoscope are detected using an X-ray examination device, a magnetic resonance image diagnosis device, etc. In addition, investment needs to be made on expensive equipment.

Furthermore, while the location of the distal end and the shape of the insertion unit can be specified using a location and shape detection device in the endoscopic device disclosed in Patent Document 1, the endoscopic device does not allow an observer to find out a location inside a living body, in real time, during a surgery.

An example object of the present invention is to provide a location estimation apparatus, a location estimation method, and a computer readable recording medium that specify a location in a living body using a living-body internal image.

Solution to the Problems

In order to achieve the above-described object, a location estimation apparatus according to an example aspect of the present invention includes:

a feature amount extraction unit configured to extract a feature amount of a living-body internal image, from the living-body internal image captured using an endoscope;

a similarity degree output unit configured to output similarity degrees with a plurality of locations inside a living body using the feature amount; and an estimation unit configured to estimate a location of the captured living-body internal image inside the living body using the similarity degrees.

In addition, in order to achieve the above-described object, a location estimation method according to an example aspect of the present invention includes:

a feature amount of a living-body internal image from the living-body internal image captured using an endoscope;

outputting similarity degrees with a plurality of locations inside a living body using the feature amount; and estimating a location of the captured living-body internal image inside the living body using the similarity degrees.

Furthermore, in order to achieve the above-described object, a computer readable recording medium that includes a program recorded thereon according to an example aspect of the present invention includes recorded thereon a program including instructions that cause a computer to carry out:

extracting a feature amount of the living-body internal image from a living-body internal image captured using an endoscope;

outputting similarity degrees with a plurality of locations inside a living body using the feature amount; and estimating a location of the captured living-body internal image inside the living body using the similarity degrees.

Advantageous Effects of the Invention

As described above, according to the present invention, a location in a living body can be estimated using a living-body internal image.

BRIEF DESCRIPTION OF THE DRAWINGS

FIG. 4 is a diagram for describing one example of results of similarity degrees.

EXAMPLE EMBODIMENT

Example Embodiment

Figure 1:
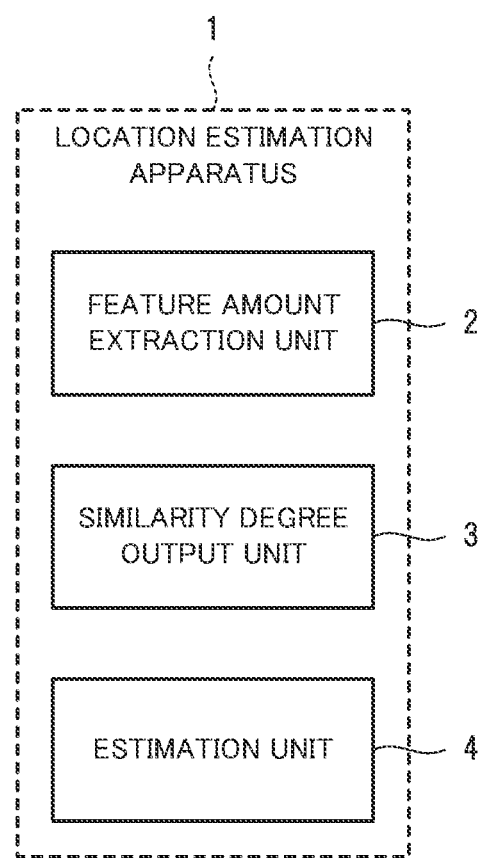
FIG. 1 is a diagram for describing one example of a location estimation apparatus.

In the following, an example embodiment of the present invention will be described with reference to FIGS. 1 to 10.
[Apparatus Configuration]
First, a configuration of a location estimation apparatus 1 in the present example embodiment will be described with reference to FIG. 1. FIG. 1 is a diagram for describing one example of the location estimation apparatus.

The location estimation apparatus 1 illustrated in FIG. 1 is an apparatus that estimates a location in a living body using a living-body internal image. Furthermore, as illustrated in FIG. 1, the location estimation apparatus 1 includes a feature amount extraction unit 2, a similarity degree output unit 3, and an estimation unit 4.

Among these units, the feature amount extraction unit 2 extracts, from a living-body internal image captured using an endoscope, a feature amount of the living-body internal image. The similarity degree output unit 3 outputs similarity degrees with a plurality of locations inside a living body using the feature amount. The estimation unit 4 estimates a location of the captured living-body internal image inside the living body using the similarity degrees.

In such a manner, in the present example embodiment, an image capture location inside a living body can be estimated using only a captured living-body internal image. Accordingly, an image capture location inside a living body can be estimated without using an X-ray examination device, a magnetic resonance image diagnosis device, or the like, and thus investment does not need to be made on expensive equipment.

Figure 2:
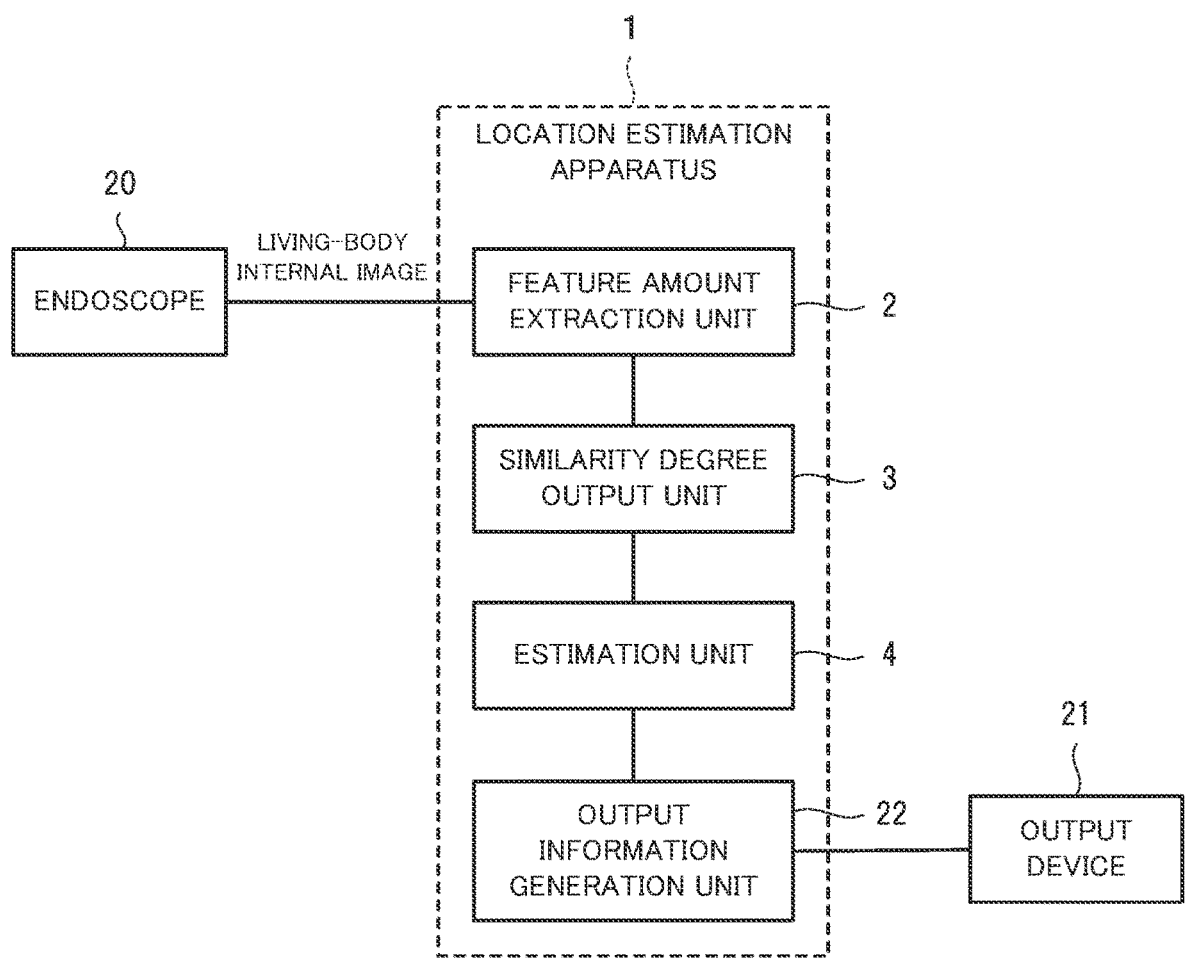
FIG. 2 is a diagram for describing one example of a system including the location estimation apparatus.

In addition, since an image capture location inside a living body can be estimated using only a captured living-body internal image, surgery can be prevented from becoming cumbersome. Furthermore, it is possible to allow an observer to find out a location inside a living body during surgery, in real time.
[System Configuration]
Next, the configuration of the location estimation apparatus 1 in the present example embodiment will be more specifically described with reference to FIG. 2. FIG. 2 is a diagram for describing one example of a system including the location estimation apparatus.

As illustrated in FIG. 2, the system in the present example embodiment includes the location estimation apparatus 1, which estimates an image capture location inside a living body, an endoscope 20, and an output device 21. Furthermore, in FIG. 2, the location estimation apparatus 1 includes an output information generation unit 22 in addition to the feature amount extraction unit 2, the similarity degree output unit 3, and the estimation unit 4.

The endoscope 20 transmits, to the location estimation apparatus 1 connected thereto, a living-body internal image obtained by capturing an image of the inside of a living body. For example, the endoscope 20 includes an insertion unit that is inserted into the living body, an image-capturing unit that is provided in the distal end-side of the insertion unit, an operation unit for operating the bending of the insertion unit, the capturing of images by the image-capturing unit, etc., and a connection unit that connects the endoscope 20 and the location estimation apparatus 1. In addition, besides the image-capturing unit, the endoscope 20 includes an illumination unit, a nozzle (nozzles) used for feeding air and water and for suction, a forceps port, etc., in the distal end-side of the insertion unit.

The output device 21 acquires, from the output information generation unit 22, output information (to be described later) converted into formats that can be output, and outputs images, sound, etc., generated on the basis of the output information. The output device 21, for example, includes an image display device utilizing liquid crystals, organic electroluminescence (EL), or a cathode ray tube (CRT), and further includes a sound output device such as a speaker, and the like. Note that the output device 21 may also be a printing device such as a printer.

The feature amount extraction unit 2 extracts a feature amount from the living-body internal image using the living-body internal image captured by the endoscope 20. Specifically, the feature amount extraction unit 2 first acquires living-body internal images captured in a time series using the endoscope 20. Next, the feature amount extraction unit 2 extracts a feature amount corresponding to a target part inside the living body from the acquired living-body internal images.

In the case of the large intestine for example, as the feature amount of a living-body internal image, the use of one or more among: whether or not intestinal folds are present; fold size; the positional relationship between folds; intestinal tract diameter; intestinal shape; and whether or not the ileocecal valve is present can be conceived. Specifically, parts of the large intestine have the following characteristics: the cecum includes the ileocecal valve (the Bauhin's valve); the ascending colon has a wide tract diameter and has large, deep folds; the transverse colon has folds with triangle-like shapes; and the descending colon has shallow folds and has a relatively narrow tract diameter. Furthermore, the hepatic flexure, the splenic flexure, the sigmoid colon, the rectum, the anus, etc., in the large intestine have their respective characteristics. In particular, the sigmoid colon is characterized for bending in a complex manner, and the rectum is characterized for having a large volume and space.

Note that local binary patterns (LBP) is known as a method for extracting image feature amounts. For example, see the document "T. Ojala, M. Pietikainen, and D. Harwood, 'Performance evaluation of texture measures with classification based on Lullback discrimination of distributions,' in the Proceedings of IEEE International Conference on Pattern Recognition, 1994.", etc.

The similarity degree output unit 3 outputs similarity degrees with a plurality of locations inside the living body using the feature amount. Specifically, (1) the similarity degree output unit 3 calculates similarity degrees using the feature amount extracted by the feature amount extraction unit 2 and feature amounts extracted from living-body internal images stored in advance. Alternatively, (2) the similarity degree output unit 3 may use the feature amount extracted by the feature amount extraction unit 2 as input, and output scores (similarity degrees) using a classifier. A neural network model, a support vector machine, or the like can be used as a classifier.

Figure 3:
FIG. 3 is a diagram for describing one example of living-body internal images.
Figure 3:
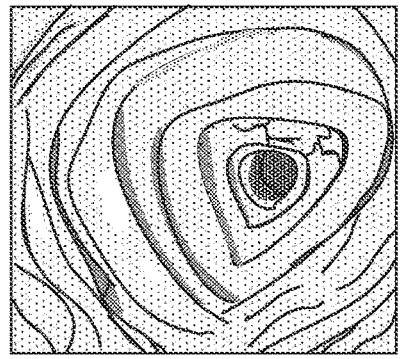
Figure 3:
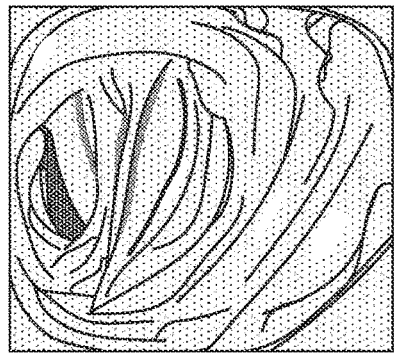
Figure 3:

(1) and (2) will be described with reference to FIG. 3. FIG. 3 is a diagram for describing one example of living-body internal images. The living-body internal images shown in FIG. 3 are captured images of the large intestine. FIG. 3A shows a captured image of the cecum, FIG. 3B shows a captured image of the ascending colon, FIG. 3C shows a captured image of the transverse colon, and FIG. 3D shows a captured image of the descending colon.

(1) will be described. In (1), first, images of the inside of the living body are captured in advance, and feature amounts extracted from the captured living-body internal images are stored in advance in a storage unit. For example, feature amounts are extracted for living-body internal images representing predetermined locations inside the large intestine, such as those shown in FIG. 3, and location identification information identifying the locations inside the large intestine (information indicating names such as the ascending colon, the transverse colon, the descending colon, the hepatic flexure, the splenic flexure, the sigmoid colon, the rectum, the anus, etc.,) and feature amounts corresponding to the locations (whether or not intestinal folds are present, fold size, intestinal tract diameter, intestinal shape, whether or not the ileocecal valve is present, etc.) are associated with one another and stored in the storage unit in advance. Note that the storage unit is provided inside or outside the location estimation apparatus 1, for example.

Subsequently, the similarity degree output unit 3 calculates similarity degrees using the feature amount extracted by the feature amount extraction unit 2 and the feature amounts extracted from the living-body internal images stored in advance. In a case in which a living-body internal image obtained by capturing an image of the ascending colon is input, for example, the results would be as shown in FIG. 4. That is, the similarity degree for the ascending colon would be highest. FIG. 4 is a diagram for describing one example of results of similarity degrees.

(2) will be described. In (2), first, images of the inside of a living body are captured in advance, and parameters of a classifier (a neural network model, for example) are learned by inputting the feature amounts extracted from the captured living-body internal images. Then, the classifier having been subjected to learning is used as the similarity degree output unit 3.

Subsequently, the similarity degree output unit 3 inputs the feature amount extracted by the feature amount extraction unit 2 and outputs scores using the classifier. The output scores indicate the likelihood of the input to the classifier belonging to each class, and can be regarded as similarity degrees. Specifically, in a case in which a living-body internal image obtained by capturing an image of the ascending colon is input, for example, the results would be as shown in FIG. 4.

The estimation unit 4 uses the similarity degrees output by the similarity degree output unit 3 and estimates the location of the captured living-body internal image inside the living body. Specifically, the estimation unit 4 acquires the similarity degrees illustrated in FIG. 4, selects the highest one of the similarity degrees, and adopts the identification information corresponding to the selected similarity degree as the location inside the living body shown by the captured living-body internal image. In the example in FIG. 4, it is estimated that an image of the ascending colon is being captured.

Furthermore, the estimation unit 4 determines the location of living-body internal images if the locations of a plurality of living-body internal images estimated within a predetermined amount of time are the same. For example, a configuration is adopted such that, if an estimation result indicating the cecum, an estimation result indicating the transverse colon, and an estimation result indicating the cecum are sequentially obtained within a predetermined amount of time, the estimation result indicating the transverse colon is not used as an estimation result. This is because it would be difficult to move an endoscope from the cecum to the transverse colon within the predetermined amount of time after an estimation result indicating the cecum is obtained. Thus, if such results are obtained, the estimation result indicating the transverse colon is determined as being an estimation error. Estimation errors can be reduced by adopting such a configuration.

Furthermore, the estimation unit 4 adopts identification information for which the similarity degree is higher than or equal to a predetermined value and which corresponds to the highest similarity degree as the location inside the living body shown by the captured living-body internal image. Estimation errors can be reduced by adopting such a configuration. Note that the predetermined value is calculated and set through experimentation and simulation.

Figure 5:
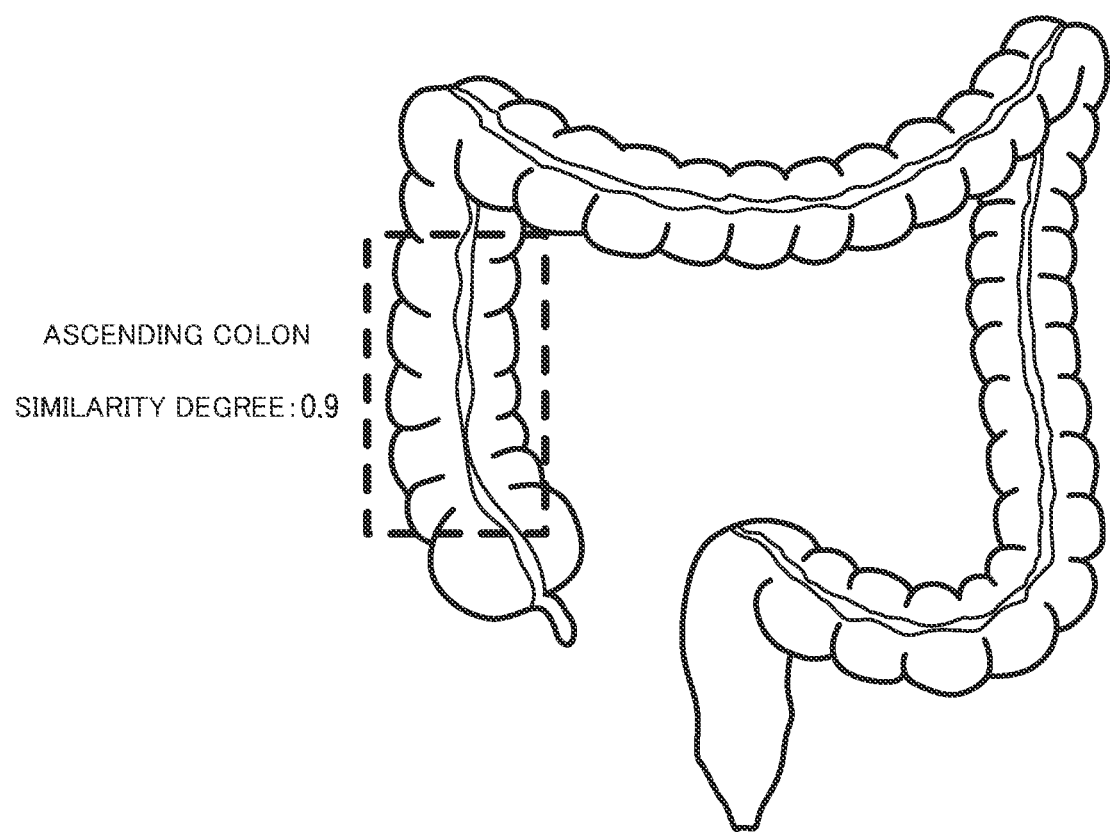
FIG. 5 is a diagram for describing one example of output of an estimation result.

The output information generation unit 22 generates display information for outputting, to the output device 21, at least one of a similarity degree and the estimated location. Specifically, the output information generation unit 22 generates output information for displaying, on the output unit 21, a display such as that illustrated in FIG. 5, and transmits the generated output information to the output device 21. FIG. 5 is a diagram for describing one example of output of an estimation result. In FIG. 5, the entire large intestine is displayed, and it is indicated that the estimated location inside the large intestine is the ascending colon.

Next, the output device 21, after acquiring the output information, outputs at least one of a screen and sound indicating the similarity degree and the estimated location on the basis of the output information. "ASCENDING COLON" indicating the estimated location in the large intestine and "SIMILARITY DEGREE: 0.9" indicating the similarity degree are displayed in the example in FIG. 5. Furthermore, the area of the ascending colon (the area in broken lines) is displayed. In addition, a configuration may also be adopted such that the area of the ascending colon blinks on and off. However, the display method is not limited to the above-described display illustrated in FIG. 5.

[Apparatus Operations]

Figure 6:
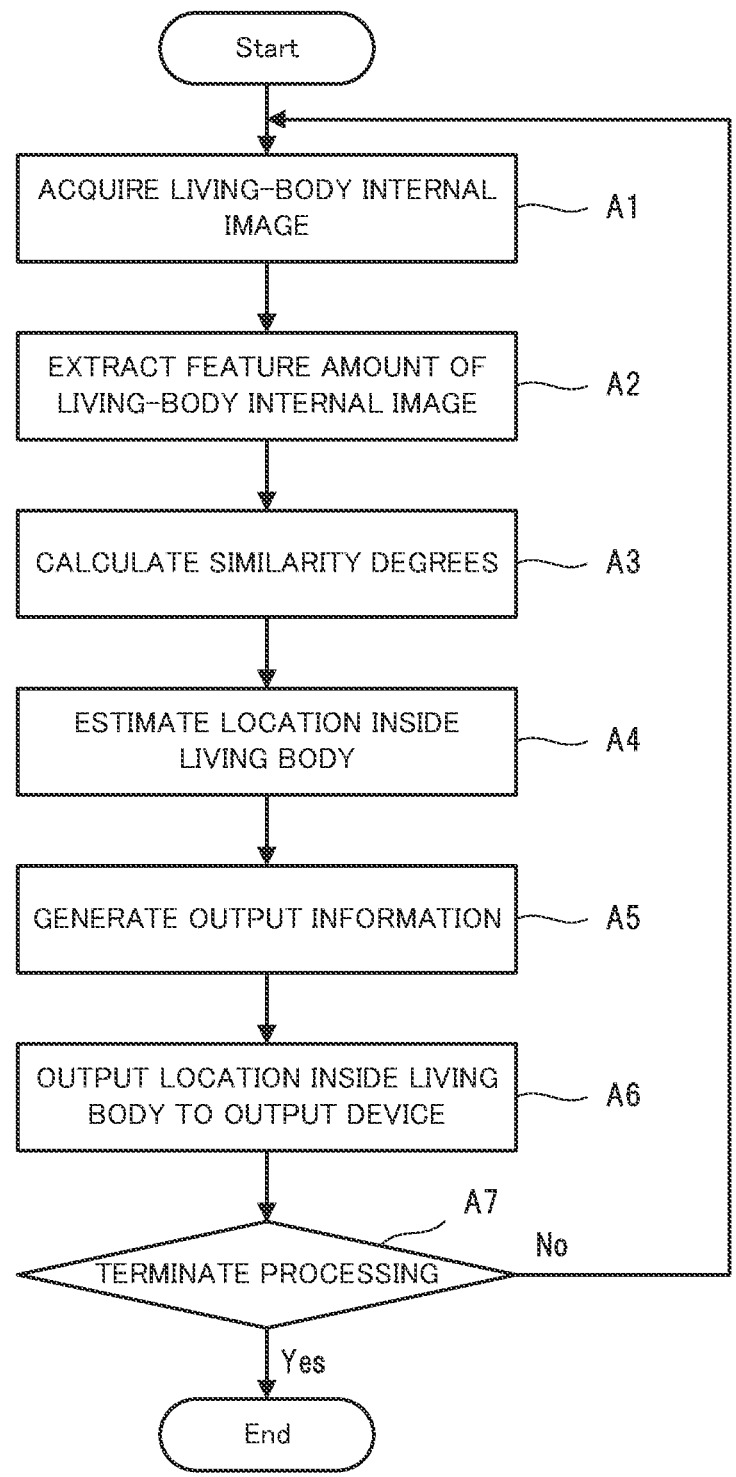
FIG. 6 is a diagram for describing one example of operations of the location estimation apparatus.

Next, operations of the location estimation apparatus 1 in the example embodiment of the present invention will be described with reference to FIG. 6. FIG. 6 is a diagram for describing one example of operations of the location estimation apparatus. FIGS. 2 to 5 will be referred to as needed in the following description. Furthermore, in the present example embodiment, a location estimation method is implemented by causing the location estimation apparatus to operate. Accordingly, the following description of the operations of the location estimation apparatus 1 is substituted for the description of the location estimation method in the present example embodiment.

As illustrated in FIG. 6, the feature amount extraction unit 2 first acquires a living-body internal image captured by the endoscope 20 (step A1). Next, the feature amount extraction unit 2 extracts a feature amount from the living-body internal image using the captured living-body internal image (step A2).

The similarity degree output unit 3 uses the feature amount of the living-body internal image and outputs similarity degrees with a plurality of locations inside the living body (step A3). Specifically, (1) the similarity degree output unit 3 calculates similarity degrees using the feature amount extracted by the feature amount extraction unit 2 and feature amounts extracted from living-body internal images stored in advance. Alternatively, (2) the similarity degree output unit 3 uses the feature amount extracted by the feature amount extraction unit 2 as input, and outputs scores using a classifier such as a neural network model or a support vector machine.

The estimation unit 4 estimates the location of the captured living-body internal image inside the living body using the similarity degrees output by the similarity degree output unit 3 (step A4). Furthermore, the estimation unit 4 determines the location of living-body internal images if the locations of one or more living-body internal images estimated within a predetermined amount of time are the same.

The output information generation unit 22 generates display information for outputting, to the output device 21, at least one of a similarity degree and the estimated location (step A5). The output device 21, after acquiring the output information, outputs at least one of a screen and sound indicating the similarity degree and the estimated location on the basis of the output information (step A6).

Next, the location estimation apparatus 1 terminates the estimation of location if an instruction to terminate processing for estimating location is acquired (step A7: Yes). Furthermore, if the processing for estimating location is to be continued (step A7: No), the location estimation apparatus 1 moves on to step A1 and continues the estimation of location.

The operations of the location estimation apparatus 1 will be specifically described with reference to FIGS. 7 and 8.

Figure 7:
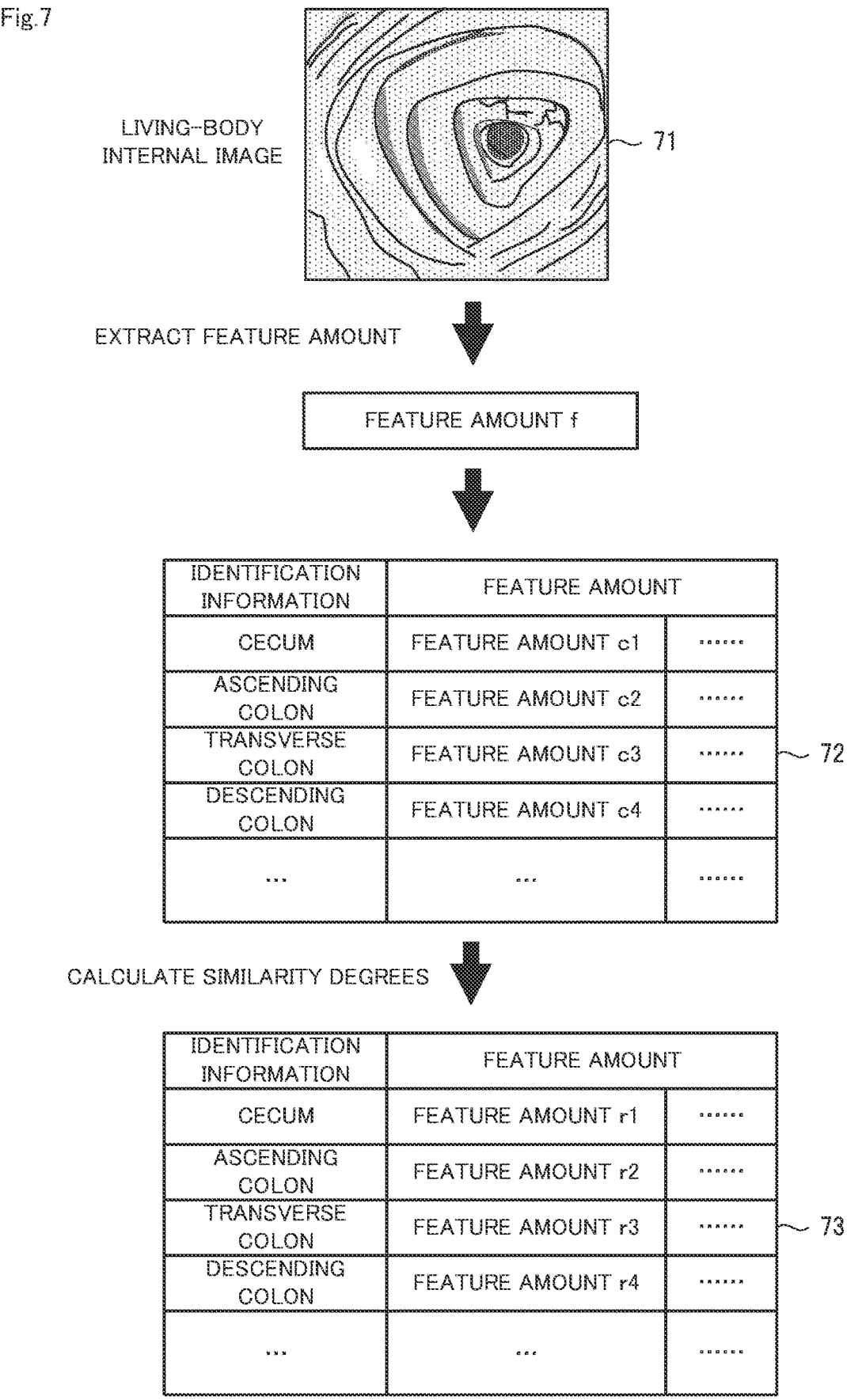
FIG. 7 is a diagram for describing one example of operations in a case in which a typical living-body internal image is used.
Figure 8:
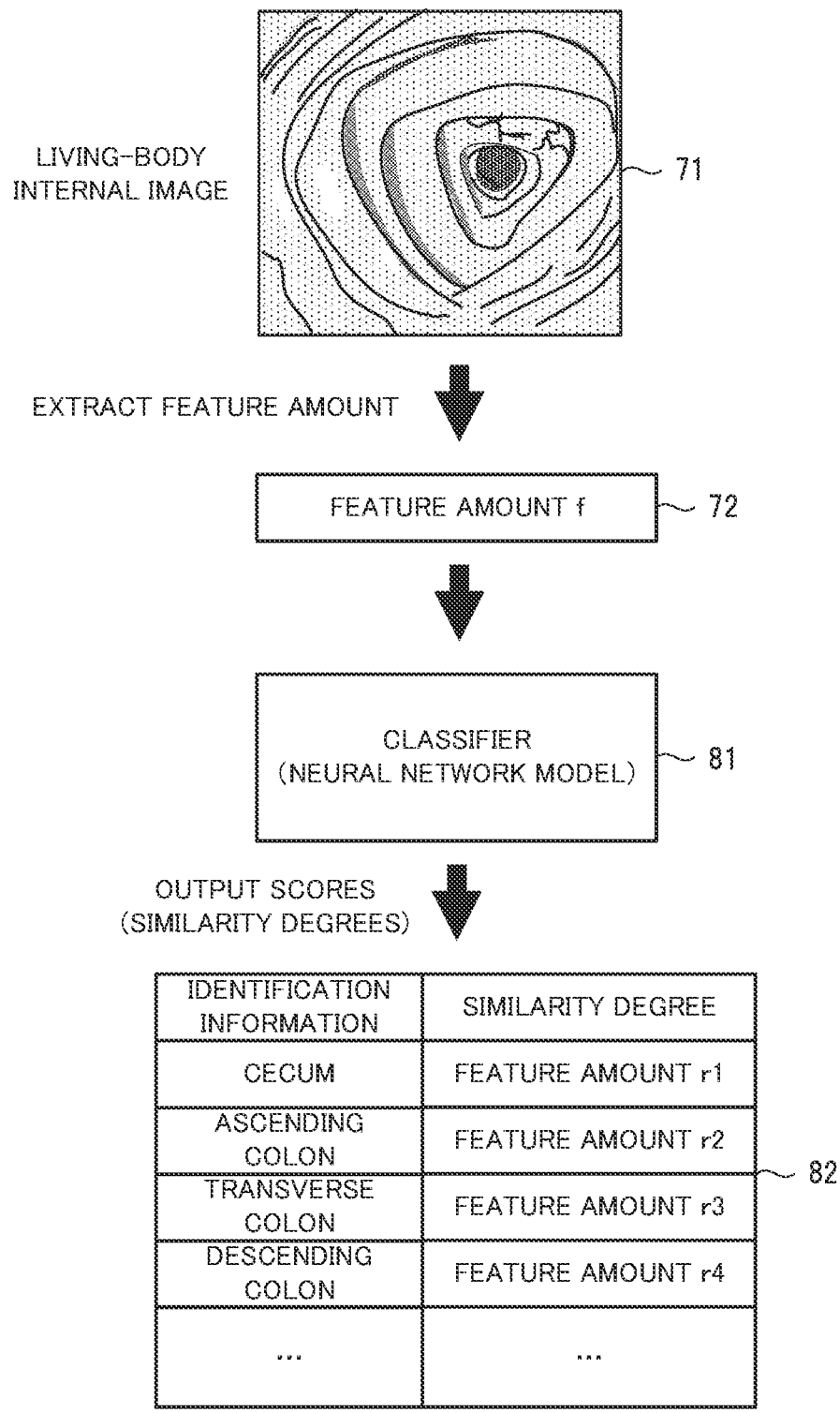
FIG. 8 is a diagram for describing one example of operations in a case in which a classifier is used.

FIG. 7 is a diagram for describing one example of operations in a case in which typical living-body internal images are used. FIG. 8 is a diagram for describing one example of operations in a case in which a classifier is used.

First, with reference to FIG. 7, a case will be described in which (1) the similarity degree output unit 3 calculates similarity degrees using a feature amount f extracted by the feature amount extraction unit 2 and feature amounts c (c1, c2, c3, c4, . . . ) extracted from typical living-body internal images stored in advance.

In step A1, the feature amount extraction unit 2 acquires a living-body internal image 71, which is a captured image of the ascending colon. Next, in step A2, the feature amount extraction unit 2 calculates a feature amount f using the captured living-body internal image 71.

Next, in step A3, the similarity degree output unit 3 calculates a similarity degree for each piece of identification information ushing the feature amount f of the living-body internal image having depth information associated therewith and feature amount information 72 including the feature amounts c (c1, c2, c3, c4, . . . ) extracted from the typical living-body internal images stored in advance. Consequently, similarity degree information 73 is obtained. The similarity degree information 73 indicates results as shown in FIG. 4, for example. That is, the similarity degree for the ascending colon would be highest.

Next, in step A4, the estimation unit 4 estimates the location of the captured living-body internal image inside the living body using the similarity degree information 73. Specifically, the estimation unit 4 selects the highest one of the similarity degrees acquired, and adopts the identification information corresponding to the selected similarity degree as the location inside the living body shown by the captured living-body internal image. Note that, in step A4, the estimation unit 4 determines the location of living-body internal images if the locations of one or more living-body internal images estimated within a predetermined amount of time are the same.

Next, in step A5, the output information generation unit 22 generates output information for displaying, on the output unit 21, a display such as that illustrated in FIG. 5, and transmits the generated output information to the output device 21. Next, in step A6, the output device 21, after acquiring the output information, outputs at least one of a screen and sound indicating the similarity degree and the estimated location on the basis of the output information.

Next, with reference to FIG. 8, a case will be described in which (2) a feature amount extracted by the feature amount extraction unit 2 is used as input, and scores are output using a classifier. The processing from step A1 to step A2 and the processing from step A5 to step A7 are not described due to being the same.

In step A3 in (2), the similarity degree output unit 3 uses a feature amount f of a living-body internal image as input, and calculates a score for each piece of identification information using a classifier 81. Consequently, the similarity degree output unit 3 acquires similarity degree information 82. The similarity degree information 82 indicates results as shown in FIG. 4, for example. That is, the similarity degree for the ascending colon would be highest.

Next, in step A4, the estimation unit 4 estimates the location of the captured living-body internal image inside the living body using the similarity degree information 82. Specifically, the estimation unit 4 selects the highest one of the similarity degrees acquired, and adopts the identification information corresponding to the selected similarity degree as the location inside the living body shown by the captured living-body internal image. Note that, in step A4, the estimation unit 4 determines the location of living-body internal images if the locations of one or more living-body internal images estimated within a predetermined amount of time are the same. Furthermore, in step A4, the estimation unit 4 adopts identification information for which the similarity degree is higher than or equal to a predetermined value and which corresponds to the highest similarity degree as the location inside the living body shown by the captured living-body internal image.

[Modification]

A modification will be described. The location estimation apparatus 1 in the modification calculates similarity degrees, estimates a location inside a living body, generates output information, and outputs the location inside the living body to the output device 21 on the basis of the output information, on the condition that depth information is extracted by the feature amount extraction unit 2.

In the modification, the feature amount extraction unit 2 further extracts, as a feature amount, depth information of the inside of a living body in a living-body internal image. Specifically, the feature amount extraction unit 2 first estimates the depth (distance) from the endoscope lens to the intestinal wall surface. Next, the feature amount extraction unit 2 associates a fold appearing in the living-body internal image and the distance from the endoscope lens to the intestinal wall surface with one another, and generates depth information. Note that the processing for extracting the depth information may be separated from the feature amount extraction unit 2.

The depth information is calculated using a technique such as that disclosed in the document "K. Karsch, C. Liu, and S. B. Kang, 'Depth extraction from video using non-parametric sampling,' in European Conference on Computer Vision. Springer, 2012, pp. 775-788.", for example.

Furthermore, in the modification, the similarity degree output unit 3 calculates similarity degrees using a feature amount of a living-body internal image having depth information. Specifically, the similarity degree output unit 3 determines whether or not depth information is present, and uses the feature amount of the living-body internal image and calculates similarity degrees if depth information is extracted. Note that the similarity degree output unit 3 does not calculate similarity degrees if depth information cannot be extracted.

If depth information is extracted, the estimation unit 4 estimates a location inside the living body using the calculated similarity degrees. Next, the output information generation unit 22 generates output information and outputs the output information to the output device 21. The output device 21 outputs the location inside the living body to the output device 21 on the basis of the output information. Note that, if depth information is not extracted by the estimation unit 4, the location estimation apparatus 1 does not output the location inside the living body to the output device 21 on the basis of the output information.

Figure 9:
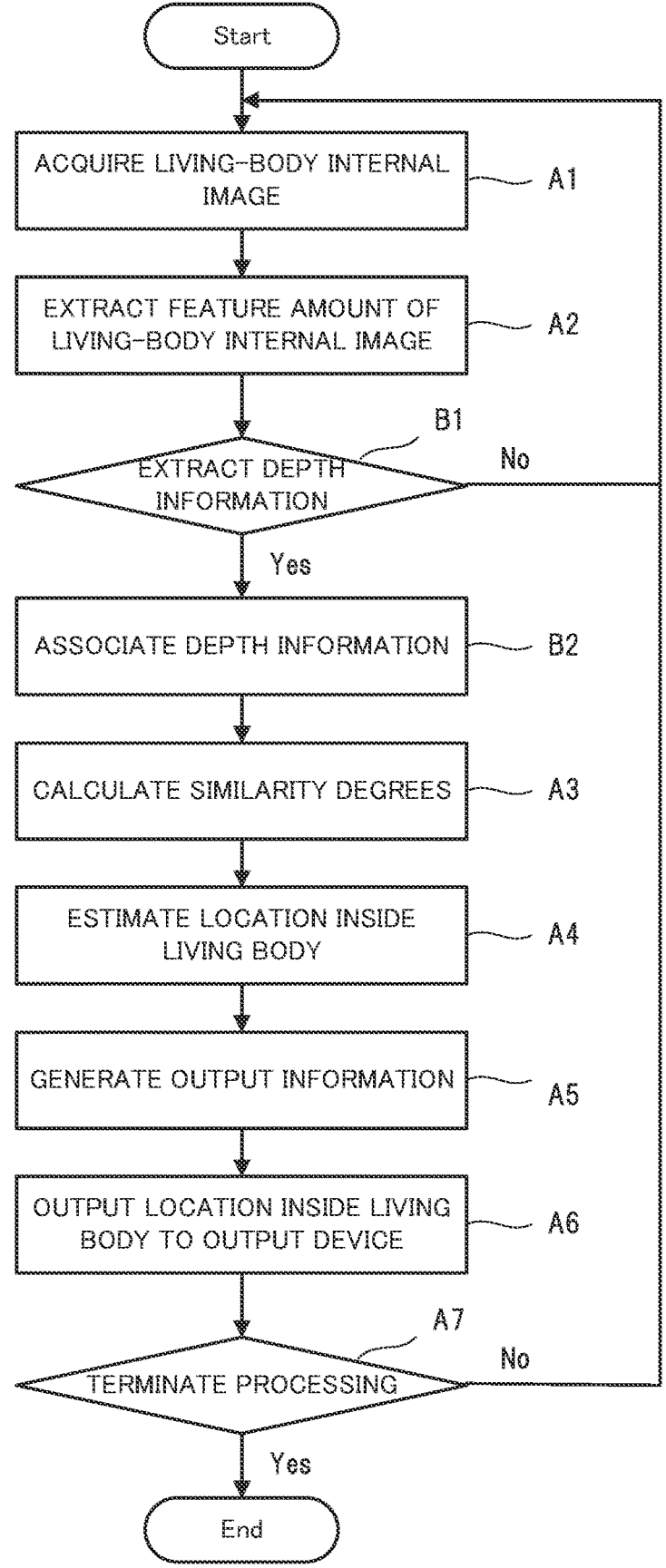
FIG. 9 is a diagram for describing one example of operations of the location estimation apparatus in a modification.

Next, operations of the location estimation apparatus 1 in the modification will be described with reference to FIG. 9. FIG. 9 is a diagram for describing one example of operations of the location estimation apparatus in the modification.

As illustrated in FIG. 9, the feature amount extraction unit 2 first acquires a living-body internal image captured by the endoscope 20 (step A1). Next, the feature amount extraction unit 2 extracts a feature amount from the living-body internal image using the captured living-body internal image (step A2). Furthermore, in step A2, the feature amount extraction unit 2 extracts, as a feature amount, depth information of the inside of the living body in the living-body internal image.

Next, the feature amount extraction unit 2 determines whether or not the living-body internal image is an image having depth information, and, if the captured living-body internal image has depth information (step B1: Yes), associates the depth information with the captured living-body internal image (step B2).

Next, if depth information is successfully extracted, the similarity degree output unit 3 outputs similarity degrees with a plurality of locations inside the living body using the feature amount of the living-body internal image having depth information associated therewith (step A3). Specifically, the similarity degree output unit 3 calculates similarity degrees using the processing in (1) or (2) described above.

The estimation unit 4 estimates the location of the captured living-body internal image inside the living body using the similarity degrees output by the similarity degree output unit 3 (step A4). Furthermore, the estimation unit 4 determines the location of living-body internal images if the locations of one or more living-body internal images estimated within a predetermined amount of time are the same.

The output information generation unit 22 generates display information for outputting, to the output device 21, at least one of a similarity degree and the estimated location (step A5). The output device 21, after acquiring the output information, outputs at least one of a screen and sound indicating the similarity degree and the estimated location on the basis of the output information (step A6).

Next, the location estimation apparatus 1 terminates the estimation of location if an instruction to terminate processing for estimating location is acquired (step A7: Yes). Furthermore, if the processing for estimating location is to be continued (step A7: No), the location estimation apparatus 1 moves on to step A1 and continues the estimation of location.

Effects of Example Embodiment

As described above, according to the present example embodiment, an image capture location inside a living body can be estimated using only a captured living-body internal image. Accordingly, an image capture location inside a living body can be estimated without using an X-ray examination device, a magnetic resonance image diagnosis device, or the like, and thus investment does not need to be made on expensive equipment.

In addition, since an image capture location inside a living body can be estimated using only a captured living-body internal image, surgery can be prevented from becoming cumbersome. Furthermore, it is possible to allow an observer to find out a location inside a living body during surgery, in real time.

Furthermore, processing time can be reduced since processing is performed only on living-body internal images having depth information in processing subsequent to that performed by the feature amount extraction unit 2. Furthermore, the accuracy with which a location inside a living body is estimated can be improved.

[Program]

It suffices for the program in the example embodiment of the present invention to be a program that causes a computer to carry out steps A1 to A7 shown in FIG. 6, and steps A1, A2, B1, B2, and A3 to A7 shown in FIG. 9. By installing this program on a computer and executing the program, the location estimation apparatus and the location estimation method in the present example embodiment can be realized. In this case, the processor of the computer functions and performs processing as the feature amount extraction unit 2, the similarity degree output unit 3, the estimation unit 4, and the output information generation unit 22.

Furthermore, the program in the present example embodiment may be executed by a computer system formed from a plurality of computers. In this case, the computers may each function as one of the feature amount extraction unit 2, the similarity degree output unit 3, the estimation unit 4, and the output information generation unit 22, for example

[Physical Configuration]

Figure 10:
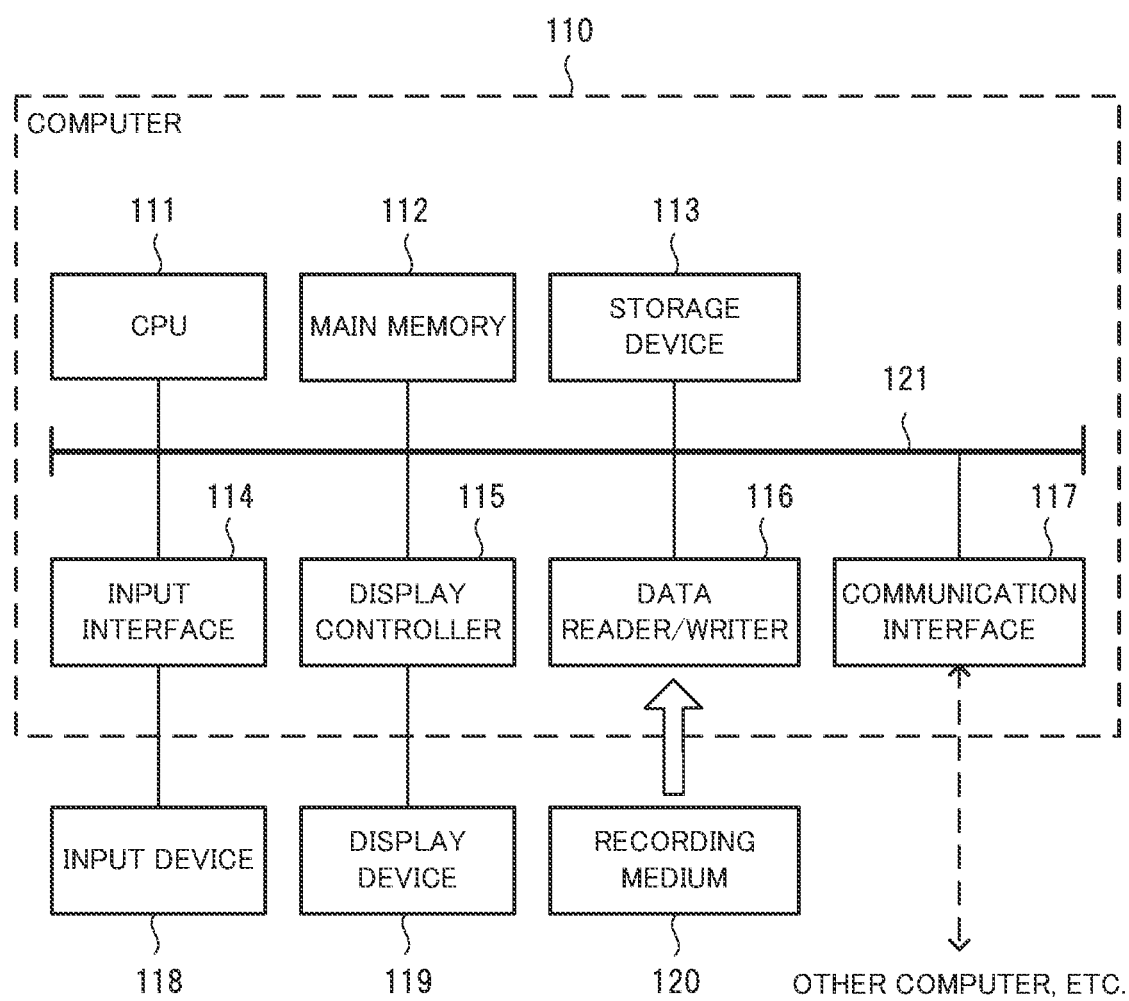
FIG. 10 is a diagram for describing one example of a computer realizing the location estimation apparatus.

Here, a computer that realizes the location estimation apparatus 1 by executing the program in the example embodiment will be described with reference to FIG. 10. FIG. 10 is a block diagram illustrating one example of a computer realizing the location estimation apparatus in the example embodiment of the present invention.

As illustrated in FIG. 10, a computer 110 includes a CPU 111, a main memory 112, a storage device 113, an input interface 114, a display controller 115, a data reader/writer 116, and a communication interface 117. These components are connected via a bus 121 so as to be capable of performing data communication with one another. Note that the computer 110 may include a graphics processing unit (GPU) or a field-programmable gate array (FPGA) in addition to the CPU 111 or in place of the CPU 111.

The CPU 111 loads the program (codes) in the present example embodiment, which is stored in the storage device 113, onto the main memory 112, and performs various computations by executing these codes in a predetermined order. The main memory 112 is typically a volatile storage device such as a dynamic random access memory (DRAM). Furthermore, the program in the present example embodiment is provided in a state such that the program is stored in a computer readable recording medium 120. Note that the program in the present example embodiment may also be a program that is distributed on the Internet, to which the computer 110 is connected via the communication interface 117.

In addition, specific examples of the storage device 113 include semiconductor storage devices such as a flash memory, in addition to hard disk drives. The input interface 114 mediates data transmission between the CPU 111 and input equipment 118 such as a keyboard and a mouse. The display controller 115 is connected to a display device 119, and controls the display performed by the display device 119.

The data reader/writer 116 mediates data transmission between the CPU 111 and the recording medium 120, and executes the reading of the program from the recording medium 120 and the writing of results of processing in the computer 110 to the recording medium 120. The communication interface 117 mediates data transmission between the CPU 111 and other computers.

Furthermore, specific examples of the recording medium 120 include a general-purpose semiconductor storage device such as a CompactFlash (registered trademark, CF) card or a Secure Digital (SD) card, a magnetic recording medium such as a flexible disk, and an optical recording medium such as a compact disk read-only memory (CD-ROM).

Note that the location estimation apparatus 1 in the present example embodiment can also be realized by using pieces of hardware corresponding to the respective units, rather than using a computer on which the program is installed. Furthermore, a part of the location estimation apparatus 1 may be realized by using a program, and the remaining part of the location estimation apparatus 1 may be realized by using hardware.

[Supplementary Note]

In relation to the above example embodiment, the following Supplementary notes are further disclosed. While a part of or the entirety of the above-described example embodiment can be expressed by (Supplementary note 1) to (Supplementary note 21) described in the following, the present invention is not limited to the following description.

(Supplementary Note 1)

A location estimation apparatus including:

a feature amount extraction unit configured to extract a feature amount of a living-body internal image, from the living-body internal image captured using an endoscope;

a similarity degree output unit configured to output similarity degrees with a plurality of locations inside a living body using the feature amount; and an estimation unit configured to estimate a location of the captured living-body internal image inside the living body using the similarity degrees.

(Supplementary Note 2)

The location estimation apparatus according to Supplementary note 1, wherein the feature amount extraction unit extracts depth information as the feature amount.

(Supplementary Note 3)

The location estimation apparatus according to Supplementary note 2, wherein if the depth information is extracted, the similarity degree output unit calculates similarity degrees using the feature amount of the living-body internal image.

(Supplementary Note 4)

The location estimation apparatus according to any one of Supplementary notes 1 to 3, wherein if locations of a plurality of the living-body internal images estimated within a predetermined amount of time are the same, the estimation unit determines the location of the living-body internal images.

(Supplementary Note 5)

The location estimation apparatus according to any one of Supplementary notes 1 to 4 further including an output information generation unit configured to generate display information for outputting, to a display device, at least one of a similarity degree and the estimated location.

(Supplementary Note 6)

The location estimation apparatus according to any one of Supplementary notes 1 to 5, wherein as the feature amount of the living-body internal image, one or more among whether or not intestinal folds are present, the size of the folds, a positional relationship between the folds, the intestinal tract diameter, the intestinal shape, and whether or not the ileocecal valve is present are used.

(Supplementary Note 7) The location estimation apparatus according to any one of Supplementary notes 1 to 6, wherein as the location inside the living body, one or more among the locations of the cecum, the ascending colon, the transverse colon, the descending colon, the sigmoid colon, the rectum, and the anus are used.

(Supplementary Note 8)

A location estimation method including:

(a) a step of extracting a feature amount of a living-body internal image, from the living-body internal image captured using an endoscope;

(b) a step of outputting similarity degrees with a plurality of locations inside a living body using the feature amount; and (c) a step of estimating a location of the captured living-body internal image inside the living body using the similarity degrees.

(Supplementary Note 9)

The location estimation method according to Supplementary note 8, wherein in the (a) step, depth information is extracted as the feature amount.

(Supplementary Note 10)

The location estimation method according to Supplementary note 9, wherein in the (b) step, if depth information is extracted, the similarity degrees are calculated using the feature amount of the living-body internal image.

(Supplementary Note 11)

The location estimation method according to any one of Supplementary notes 8 to 10, wherein in the (c) step, if locations of a plurality of the living-body internal images estimated within a predetermined amount of time are the same, the location of the living-body internal images is determined.

(Supplementary Note 12)

The location estimation method according to any one of Supplementary notes 8 to 11 further including (d) a step of generating display information for outputting, to a display device, at least one of a similarity degree and the estimated location.

(Supplementary Note 13)

The location estimation method according to any one of Supplementary notes 8 to 12, wherein as the feature amount of the living-body internal image, one or more among whether or not intestinal folds are present, the size of the folds, a positional relationship between the folds, the intestinal tract diameter, the intestinal shape, and whether or not the ileocecal valve is present are used.

(Supplementary Note 14)

The location estimation method according to any one of Supplementary notes 8 to 13, wherein as the location inside the living body, one or more among the locations of the cecum, the ascending colon, the transverse colon, the descending colon, the sigmoid colon, the rectum, and the anus are used.

(Supplementary Note 15)

A computer readable recording medium that includes a program recorded thereon, the program including instructions that cause a computer to carry out:

(a) a step of extracting, a feature amount of the living-body internal image, from a living-body internal image captured using an endoscope;

(b) a step of outputting similarity degrees with a plurality of locations inside a living body using the feature amount; and (c) a step of estimating a location of the captured living-body internal image inside the living body using the similarity degrees.

(Supplementary Note 16)

The computer readable recording medium according to Supplementary note 15, wherein in the (a) step, depth information is extracted as the feature amount.

(Supplementary Note 17)

The computer readable recording medium according to Supplementary note 16, wherein in the (b) step, if depth information is extracted, the similarity degrees are calculated using the feature amount of the living-body internal image.

(Supplementary Note 18)

The computer readable recording medium according to any one of Supplementary notes 15 to 17, wherein the (c) step, if locations of a plurality of the living-body internal images estimated within a predetermined amount of time are the same, the location of the living-body internal images is set in determined.

(Supplementary Note 19)

The computer readable recording medium according to any one of Supplementary notes 15 to 18, wherein the computer is caused to carry out (d) a step of generating display information for outputting, to a display device, at least one of a similarity degree and the estimated location.

(Supplementary Note 20)

The computer readable recording medium according to any one of Supplementary notes 15 to 19, wherein as the feature amount of the living-body internal image, one or more among whether or not intestinal folds are present, the size of the folds, a positional relationship between the folds, the intestinal tract diameter, the intestinal shape, and whether or not the ileocecal valve is present are used.

(Supplementary Note 21)

The computer readable recording medium according to any one of Supplementary notes 15 to 20, wherein as the location inside the living body, one or more among the locations of the cecum, the ascending colon, the transverse colon, the descending colon, the sigmoid colon, the rectum, and the anus are used.

The present invention has been described with reference to an example embodiment above, but the present invention is not limited to the above-described example embodiment. Within the scope of the present invention, various changes that could be understood by a person skilled in the art could be applied to the configurations and details of the present invention.

This application is based upon and claims the benefit of priority from Japanese application No. 2018-175740, filed on Sep. 20, 2018, the disclosure of which is incorporated herein in its entirety by reference.

INDUSTRIAL APPLICABILITY

As described above, according to the present invention, a location in a living body can be estimated using a living-body internal image. The present invention is useful in fields in which a location in a living body needs to be estimated using a living-body internal image.

REFERENCE SIGNS LIST

1 Location estimation apparatus
2 Feature amount extraction unit
3 Similarity degree output unit
4 Estimation unit
20 Endoscope
21 Output device
22 Output information generation unit
110 Computer
111 CPU
112 Main memory
113 Storage device
114 Input interface
115 Display controller
116 Data reader/writer
117 Communication interface
118 Input equipment
119 Display device
120 Recording medium
121 Bus

What is claimed is:

1. A location estimation apparatus comprising:
a processor; and
a memory storing instructions executable by the processor to:
estimate a distance from a lens of an endoscope to an intestinal wall surface;
associate the distance and a fold appearing in a living-body internal image captured using the endoscope;
generate, as a feature amount of the living-body internal image, depth information from the living-body internal image based on the fold associated with the distance;
output similarity degrees with a plurality of locations inside a living body using the feature amount; and
estimate a location of the captured living-body internal image inside the living body using the similarity degrees.

2. The location estimation apparatus according to claim 1, wherein the instructions are executable by the processor to further:
generate display information for outputting, to a display device, at least one of the similarity degrees and the estimated location.

3. The location estimation apparatus according to claim 1, wherein
one or more among a size of the fold, an intestinal tract diameter, an intestinal shape, and whether or not an ileocecal valve is present are also used as the feature amount of the living-body internal image.

4. The location estimation apparatus according to claim 1, wherein
one or more among locations of a cecum, an ascending colon, a transverse colon, a descending colon, a sigmoid colon, a rectum, and an anus are used as the location inside the living body.

5. A location estimation method comprising:
estimating, by a processor, a distance from a lens of an endoscope to an intestinal wall surface;
associating, by the processor, the distance and a fold appearing in a living-body internal image captured using the endoscope;
generating, by the processor and as a feature amount of the living-body internal image, depth information from the living-body internal image based on the fold associated with the distance;
outputting, by the processor, similarity degrees with a plurality of locations inside a living body using the feature amount; and
estimating, by the processor, a location of the captured living-body internal image inside the living body using the similarity degrees.

6. The location estimation method according to claim 5, further comprising
generating display information for outputting, to a display device, at least one of the similarity degrees and the estimated location.

7. The location estimation method according to claim 5, wherein
one or more among a size of the fold, an intestinal tract diameter, an intestinal shape, and whether or not an ileocecal valve is present are also used as the feature amount of the living-body internal image.

8. The location estimation method according to claim 5, wherein
one or more among locations of a cecum, an ascending colon, a transverse colon, a descending colon, a sigmoid colon, a rectum, and an anus are used as the location inside the living body.

9. A non-transitory computer readable recording medium storing a program including instructions that cause a computer to carry out:
estimating a distance from a lens of an endoscope to an intestinal wall surface;
associating the distance and a fold appearing in a living-body internal image captured using the endoscope;
generating, as a feature amount of the living-body internal image, depth information from the living-body internal image based on the fold associated with the distance;
outputting similarity degrees with a plurality of locations inside a living body using the feature amount; and
estimating a location of the captured living-body internal image inside the living body using the similarity degrees.

* * * * *